United States Patent
Morgan

(10) Patent No.: US 6,331,290 B1
(45) Date of Patent: Dec. 18, 2001

(54) FORMATION OF MONODISPERSE PARTICLES

(75) Inventor: George Richard Morgan, Didcot (GB)

(73) Assignee: Accentus PLC, Didot (GB)

( * ) Notice: Subject to any disclaimer, the term of this patent is extended or adjusted under 35 U.S.C. 154(b) by 0 days.

(21) Appl. No.: 09/444,506

(22) Filed: Nov. 22, 1999

(30) Foreign Application Priority Data

Nov. 27, 1998 (GB) .................................. 9825883

(51) Int. Cl.⁷ .................................. A61K 9/14; B05B 1/08
(52) U.S. Cl. .................................. 424/46; 521/50; 424/43; 424/45; 424/489; 239/99; 239/101
(58) Field of Search .................................. 521/50; 424/489, 424/43, 45, 46; 239/99, 101

(56) References Cited

U.S. PATENT DOCUMENTS

| | | | |
|---|---|---|---|
| 3,775,058 | 11/1973 | Bush | 23/230 R |
| 4,746,466 | 5/1988 | Takahashi | 261/30 |
| 5,836,515 | 11/1998 | Fonzes | 239/102.2 |

FOREIGN PATENT DOCUMENTS

| | | |
|---|---|---|
| 2831970 | 2/1980 | (DE) . |
| 3516144 | 11/1986 | (DE) . |
| 0532349 | 3/1993 | (EP) . |
| 0656230 | 6/1995 | (EP) . |
| 92/11050 | 7/1992 | (WO) . |
| WO 94/20204 | 9/1994 | (WO) . |
| WO 97/48557 | 12/1997 | (WO) . |
| 98/26827 | 6/1998 | (WO) . |

*Primary Examiner*—Samuel A. Acquah
(74) *Attorney, Agent, or Firm*—William H. Holt

(57) ABSTRACT

Particles are made from a liquid feedstock (13) containing a pharmaceutical composition, the particles either being solid or being liquid droplets in an aerosol, by supplying the feedstock to an electronic droplet generator (18), and collecting the droplets in a holding chamber (20). Evaporation of the solvent creates particles which may be trapped using a cyclone (22). The generator (18) comprises a feed chamber (28) to which the feedstock is supplied, a dispensing chamber (30) having an inlet port communicating with the feed chamber and having an outlet port (34), and electronic means (36) for repeatedly applying a pressure pulse to the feed chamber and a pressure pulse to the dispensing chamber so that a droplet is ejected. Each droplet is of volume substantially equal to that of the dispensing chamber, so the particles can be substantially monodisperse, and may be of diameter in the range 0.1–20 μm.

8 Claims, 1 Drawing Sheet

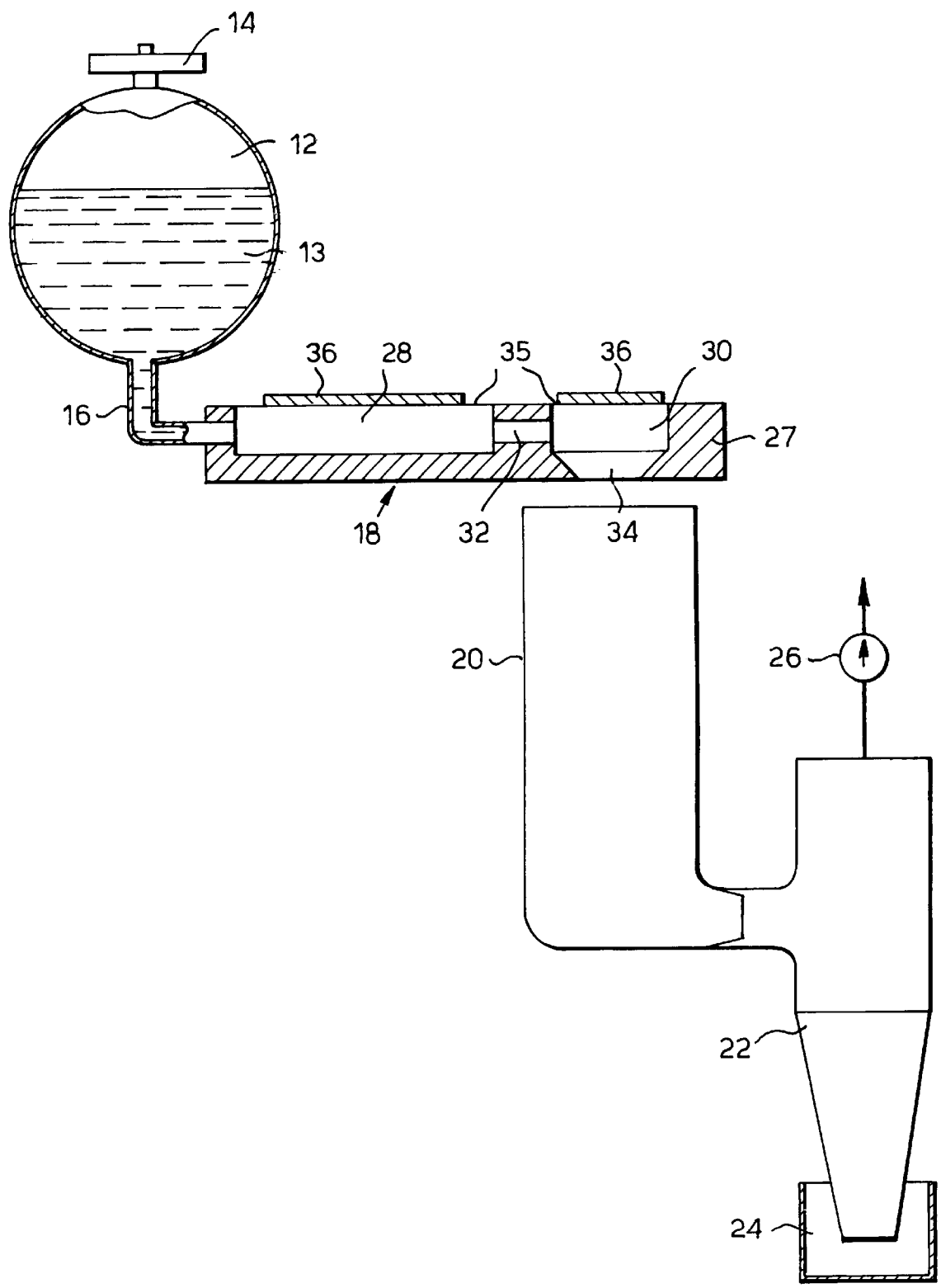

FORMATION OF MONODISPERSE PARTICLES

The present invention relates to a method and an apparatus for making particles from a liquid feedstock, the particles either being solid or being liquid droplets in an aerosol, and being substantially monodisperse.

Producing particles which are of diameter less than say 5 μm is of particular importance for pharmaceutical applications, as powders comprising such small particles provide advantages. For example they dissolve more easily because of their large surface area; such small particles allow flexibility in the packaging of drugs and provide greater freedom in selecting the mode of delivery; small particles allow more precise dosing, enabling the exact quantity of an active ingredient to be achieved; and for efficient drug delivery via the respiratory tract it is desirable to use an aerosol of particles with a limited size range to ensure particles are inhaled and reach the desired part of the the body. Known methods for producing such small particles include milling, and spray-drying. Milling involves mixing an active drug with appropriate excipients, and grinding the mixture in a suitable mill; however it is difficult to produce monodisperse particles, and furthermore the milling generates heat which may alter the structure of the active ingredient. Spray drying requires a liquid feedstock to be sprayed into a tank of hot gas so the solvent evaporates, leaving dry particles which can be collected. It is again difficult to obtain monodisperse particles, because the spray is polydisperse. A monodisperse particle fraction can in each case be obtained by sieving, although this decreases the yield.

According to the present invention there is provided a method for making particles from a liquid feedstock comprising a pharmaceutical composition and a solvent, the method comprising supplying the feedstock to an electronic droplet generator, the generator comprising a feed chamber to which the feedstock is supplied, a dispensing chamber having an inlet port communicating with the feed chamber and having an outlet port, and electronic means for applying a pressure pulse to the feed chamber and a pressure pulse to the dispensing chamber so that substantially all the liquid feedstock in the dispensing chamber is ejected at once, to form a droplet of the liquid feedstock, the electronic means applying the pressure pulses repeatedly, and the resulting droplets forming an aerosol in a holding chamber adjacent to the outlet port either until the solvent has evaporated, or until the droplets have been inhaled by a patient.

The pressure pulses may be provided by piezoelectric means, as in the jet printing device of WO 97/48557. The pressure pulses provided to the feed chamber and to the dispensing chamber may be simultaneous. The size of the droplets is determined primarily by the volume of the dispensing chamber, and may be 20 μm or less, for example 10 μm or 5 μm. If particles of dry powder are to be made, then when the solvent has had time to evaporate the resulting particles are trapped, for example using a cyclone. The dry particles will be smaller than the droplets, their size depending on the proportion of the liquid feedstock which evaporates, but they too will be substantially monodisperse.

In one example the liquid feedstock is generated by mixing two liquid streams immediately prior to supplying the feedstock to the generator; the mixing may be performed using a fluidic vortex mixer. A fluidic vortex mixer comprises a substantially cylindrical chamber with an axial outlet duct at the center of an end wall of the chamber, and with at least one substantially tangential inlet near the periphery of the chamber to create a spiralling flow in the chamber. A second liquid may be supplied through a second tangential inlet or through a radial inlet. Such a mixer achieves very intimate mixing of the two liquids in a short time, but does not subject the liquids to high shear.

The invention also provides an apparatus for generating particles, the apparatus comprising means to supply a liquid feedstock comprising a pharmaceutical composition and a solvent to an electronic droplet generator, the generator comprising a feed chamber to which the feedstock is supplied, a dispensing chamber having an inlet port communicating with the feed chamber and having an outlet port, and electronic means for applying a pressure pulse to the feed chamber and a pressure pulse to the dispensing chamber so that substantially all the liquid feedstock in the dispensing chamber is ejected at once, to form a droplet of the liquid feedstock, the electronic means being arranged to apply the pressure pulses repeatedly, and a holding chamber adjacent to the outlet port in which the droplets remain as an aerosol either until the solvent has evaporated, or until the droplets have been inhaled by a patient.

The apparatus may comprise a plurality of such electronic droplet generators to which the same feedstock is supplied, the droplets from the generators passing into a common holding chamber.

The invention will now be further and more particularly described, by way of example only, and with reference to the accompanying drawing which shows a partly diagrammatic sectional view of a particle generating apparatus.

Referring to the drawing, a particle generating apparatus 10 comprises a stainless-steel steel reservoir chamber 12 coupled by a capillary tube 16 to an electronic droplet generator 18. The chamber 12 contains a liquid feedstock 13 comprising a pharmaceutical product in a solvent, and is provided with a filtered air vent 14 to ensure it remains at atmospheric pressure. Droplets formed by the generator 18 pass into a holding chamber 20, in which the solvent evaporates, and the resulting particles flow through the chamber 20 into a cyclone 22, from which the trapped particles fall into a container 24. An air pump 26 (shown diagrammatically) draws an air stream through the holding chamber 20 and the cyclone 22.

The electronic droplet generator 18 is shown to a much larger scale than the other components of the apparatus 10; it may for example be less than 1 mm across. It is similar in design to that described in WO 97/48557, and comprises a block 27 defining two chambers 28, 30 connected by a channel 32. The first chamber 28, to which the feedstock 13 is supplied by the capillary tube 16, is a feed chamber; the other chamber 30 is a dispensing chamber, and has an outlet orifice 34 in one wall. One wall 35 of each chamber 28, 30 is flexible, and supports a piezoelectric actuator 36 such that application of a voltage to the actuator 36 causes it to bend, delivering a pressure pulse to the contents of the respective chamber 28 or 30.

As described in WO 97/48557, the droplet generator 18 may be made in a variety of different ways. As one example it may be made in two parts (upper and lower), made of silicon and etched to form the chambers, the resilient membrane 35 comprising a layer of polyimide coated with a titanium-copper-gold trilayer, and the two parts being bonded together by a high-pressure electrostatic bonding technique. In another, the structure is made of polyimide sheet, coated on one surface with metal, and etched using a laser, the etched sheet then being glued to another polyimide sheet.

Thus in operation of the particle generating apparatus 10, the liquid feedstock 13 is put into the reservoir chamber 12, and flows through the capillary tube 16 to fill both the feed chamber 28 and the dispensing chamber 30. Voltage signals are applied to the piezoelectric actuators 36 so that they generate pressure pulses in the chambers 28 and 30, each pulse applied to the dispensing chamber 30 causing all the liquid in that chamber 30 to be emitted through the orifice 34, so forming a droplet. It will be appreciated that the size and shape of the orifice 34 must be designed in accordance with the volume of the dispensing chamber 30 and the fluid properties (viscosity and surface tension) of the liquid feedstock, to enable droplets to be emitted sufficiently rapidly. The pressure pulses may be applied simultaneously to the chambers 28 and 30; more preferably, a pressure pulse is applied to the feed chamber 28 just before one is applied to the dispensing chamber 30, so a pressure wave passes through the channel 32 into the dispensing chamber 30 just as a pressure pulse is applied by the actuator 36 to the dispensing chamber 30. The voltage signals may be applied at a high frequency (for example between 500 Hz and 20 kHz), say 10 kHz; consequently the droplet generator 18 would emit 10,000 droplets per second.

The block 27 may be of silicon, and the chambers 28 and 30 may be generally rectangular, although as shown the dispensing chamber 30 desirably tapers towards the orifice 34. The feed chamber 28 is preferably larger than the dispensing chamber 30, as this provides the advantage of providing a buffer between the external fluid handling ducts (i.e. capillary tube 16) and the dispensing chamber 30, so that the interface between the external reservoir chamber 12 and the droplet generator 18 can use a conventional capillary tube 16, and so the design of the dispensing chamber 30 is not constrained by the need to interface with an external fluid handling duct; furthermore it enhances the rate at which the dispensing chamber 30 can be re-filled, as the feed chamber 28 can be re-filled while the dispensing chamber 30 is emitting a droplet.

The size of the resulting particles depends both on the size of the initial droplets formed by the droplet generator 18, and on the proportion of solvent in the feedstock which evaporates. For example if the initial droplets are of diameter 10 $\mu$m, and the volatile solvent constitutes 90 percent of the feedstock, the resulting particles have a volume one-tenth that of the droplets and so are of diameter about 4.6 $\mu$m. It should be appreciated that the feedstock may be a solution in the solvent, or may comprise a suspension of particulates of at least some of the ingredients in the solvent, as long as the particulates are sufficiently small.

In a modification, the cyclone 22, the trap 24 and the pump 26 are omitted, and a mouth piece (not shown) is attached directly to the outlet from the holding chamber 20. When the patient breathes in through the mouth piece, he sucks the aerosol of particles in the holding chamber 20 into his lungs. The mouth piece may incorporate a valve so that the contents of the holding chamber 30 are released in response to a particular stage in the patient's breathing pattern. Furthermore the apparatus 10 may incorporate means (not shown) to count the number of droplets dispensed into the holding chamber 20, and so the number of particles inhaled by the patient.

In the electronic droplet generator 18 described above, the dispensing chamber 30 has a single outlet orifice 34. In a modification the dispensing chamber 30 may have a plurality of orifices, for example two orifices, which may be of different diameters so as to generate droplets of two different sizes, and hence particles of two different sizes. Alternatively a particle generating apparatus might include several electronic droplet generators 18, each receiving a liquid feedstock from a common reservoir 12, and each emitting droplets into a common holding chamber 20. Several such electronic droplet generators 18 may be defined in a single block of material, for example silicon.

In some cases the manufacturing process may require two or more liquid feedstocks to be mixed. This mixing may be performed using, for example, a fluidic vortex mixer to mix the liquids before they are supplied to the feed chamber 28 of the or each electronic droplet generator 18. Alternatively the mixing may take place after formation of the droplets, the different liquid feedstocks 13 being supplied to respective electronic droplet generators 18, the droplet generators 18 being synchronized, and being arranged so that the droplets are on intersecting trajectories. The generators 18 may be arranged so that droplets of the different feedstocks coalesce, or may be arranged such that particles (formed by evaporation of the solvent from one such liquid feedstock) are coated by droplets of a second liquid feedstock. After evaporation of the solvent the resulting particles in the former case comprise a mixture of the ingredients from the different feedstocks, whereas in the latter case the resulting particles comprise a core of ingredients from one feedstock coated with ingredients from another feedstock.

It will be appreciated that a droplet or particle generator may differ from that described above, while falling within the scope of the present invention. For example, when forming dry particles, it may be preferable to provide a source of heat to ensure the solvent evaporates within the holding chamber 20. A different collection device may be used, in place of the cyclone 22.

I claim

1. A method for making particles from a liquid feedstock comprising a pharmaceutical composition and a solvent, the method comprising supplying the feedstock to an electronic droplet generator, the generator comprising a feed chamber to which the feedstock is supplied, a dispensing chamber having an inlet port communicating with the feed chamber and having an outlet port, and electronic means for applying a pressure pulse to the feed chamber and a pressure pulse to the dispensing chamber so that substantially all the liquid feedstock in the dispensing chamber is ejected at once, to form a droplet of the liquid feedstock, the electronic means applying the pressure pulses repeatedly, and the resulting droplets forming an aerosol in a holding chamber adjacent to the outlet port either until the solvent has evaporated, or until the droplets have been inhaled by a patient.

2. A method as claimed in claim 1 wherein the pressure pulses are provided by piezoelectric means.

3. A method as claimed in claim 2, wherein the resulting particles are trapped, after the solvent has evaporated.

4. An apparatus for generating particles, the apparatus comprising means to supply a liquid feedstock comprising a pharmaceutical composition and a solvent to an electronic droplet generator, the generator comprising a feed chamber to which the feedstock is supplied, a dispensing chamber having an inlet port communicating with the feed chamber and having an outlet port, and electronic means for applying a pressure pulse to the feed chamber and a pressure pulse to the dispensing chamber so that substantially all the liquid feedstock in the dispensing chamber is ejected at once, to form a droplet of the liquid feedstock, the electronic means being arranged to apply the pressure pulses repeatedly, and a holding chamber adjacent to the outlet port in which the droplets remain as an aerosol either until the solvent has evaporated, or until the droplets have been inhaled by a patient.

5. An apparatus as claimed in claim 4 which comprises a plurality of such electronic droplet generators to which the same feedstock is supplied, the droplets from the generators passing into a common holding chamber.

6. An apparatus as claimed in claim 5 wherein a plurality of electronic droplet generators are defined on a single block of material.

7. An apparatus as claimed in claim 4 also comprising a trap for trapping the resulting particles after the solvent has evaporated, the trap being in communication with the holding chamber.

8. An apparatus as claimed in claim 7 wherein the trap is a cyclone.

* * * * *